United States Patent [19]

Sustmann

[11] Patent Number: 4,626,238
[45] Date of Patent: Dec. 2, 1986

[54] INSERTION APPLICATOR

[75] Inventor: Scarlet Sustmann, Viersen, Fed. Rep. of Germany

[73] Assignee: Henkel Kommanditgesellschaft auf Aktien, Duesseldorf, Fed. Rep. of Germany

[21] Appl. No.: 729,597

[22] Filed: May 2, 1985

[30] Foreign Application Priority Data

May 11, 1984 [DE] Fed. Rep. of Germany ....... 3417519

[51] Int. Cl.⁴ ............................................. A61F 13/20
[52] U.S. Cl. ..................................................... 604/15
[58] Field of Search ...................................... 604/15, 16

[56] References Cited

U.S. PATENT DOCUMENTS

| 2,879,769 | 3/1959 | Gordon et al. | 604/15 |
| 4,273,125 | 6/1981 | Sakurai | 604/16 |
| 4,291,696 | 9/1981 | Ring | 604/16 |
| 4,398,532 | 8/1983 | Sweeney, III | 604/16 |
| 4,447,222 | 5/1984 | Sartinoranont | 604/15 |

Primary Examiner—John D. Yasko
Attorney, Agent, or Firm—Ernest G. Szoke; Henry E. Millson, Jr.; Mark A. Greenfield

[57] ABSTRACT

A tampon or suppository insertion applicator comprising an insertion sleeve and an injection slide whose insertable length is not greater than that of the sleeve and which has means for preventing further insertion at one end.

7 Claims, 8 Drawing Figures

INSERTION APPLICATOR

BACKGROUND OF THE INVENTION

1. Field of the Invention

This invention relates to an insertion applicator for a suppository, tampon, or similar object, comprising a tubular insertion sleeve and a plunger-like insertion slide.

2. Statement of the Related Art

The safe and convenient insertion of a catamenial tampon in feminine hygiene or of medicaments by means of a surgical tampon, suppository, or the like, is facilitated by insertion sleeves or tubes with which a plunger is associated for pushing in the tampon. The plunger generally fits in the insertion sleeve behind the tampon, although it may also be packed alongside the insertion sleeve or separately. In all instances, the volume of the tampon package, especially lengthwise, is considerably increased by the plunger. This is because the plunger has to be longer than the insertion sleeve since otherwise it would slide through the insertion tube in use and would have to be separately removed or, alternatively, the tampon could not be pushed completely out of the insertion sleeve.

For various reasons, including storage and use convenience, there is interest in reducing the package size of applicator tampons. The size of the tampon suppository, etc., itself cannot be significantly altered because it is determined by the particular application in question. Accordingly, the size and, more particularly, the length of the insertion sleeve cannot be significantly changed either.

SUMMARY OF THE INVENTION

The present invention reduces the overall volume and, more particularly, the pack length of applicator tampons, suppositories, etc., by redesigning the insertion slide. This is achieved in that the rear longitudinal end section—remote from the tampon—of the insertion slide comprises means for preventing the further insertion of the slide comprising a portion which has an external diameter which, in use, exceeds the internal diameter of the insertion sleeve but which has hardly any effect on the pack volume. According to various embodiments of the invention, the insertion slide is formed either (A) by a strip of flat material, more especially a strip of cardboard or plastic which is designed to be folded substantially centrally of its longitudinal axis and to spread open at its rear longitudinal end, or (B) by a plunger-like rod with an integrally formed offset end plate laterally of its rear longitudinal end with an external plate diameter exceeding the internal diameter of the insertion sleeve.

The effect of the insertion slide design according to the invention is that the slide only has to be longer than the insertion sleeve by the short rear end section having the increased external diameter. Since this rear end section either has to be folded or integrally formed on the side of the insertion plunger, it may be arranged adjacent the insertion sleeve in the pack without significantly increasing the volume or, above all, the length of the package.

The strip of flat material, which is designed to spread open at its rear end in use, is preferably cut substantially centrally of its longitudinal axis at that end over a length substantially corresponding to the width of the strip and, in use, is folded open transversely of the line of the cut. On insertion, the folded parts (which are strip-like, but may also be rounded off by stamping) project laterally beyond the edge of the insertion sleeve and, accordingly, cannot be pushed into the tube.

The rod according to the invention with the integrally formed end plate affording a finger depression is preferably knobbed at that longitudinal end biasing against the tampon in order to avoid damage to the tampon, suppository, or other object to be inserted and to avoid any risk of injury during insertion. In addition, it is of advantage to provide the offset end plate with an opening for the recovery cord, preferably in that edge facing the point where the depression is integrally formed with the rod. The recovery cord may thus be inserted into the opening designed to be kept facing substantially vertically upwards and, in this way, can be kept under control during insertion.

The plunger knob may also be asymmetrically formed to correspond to the offset end plate, forming a knob plate. In that case, however, the knob plate must be smaller in diameter than the internal diameter of the sleeve. In packaging, the knob plate would be arranged below the insertion end of the sleeve and the offset end plate above the rear end of the sleeve. An arrangement such as this is particularly suitable for the insertion of relatively soft objects without a recovery cord, for example suppositories. In such an instance, the knob plate may preferably be outwardly concave to complement the rear end of the suppository.

BRIEF DESCRIPTION OF THE DRAWINGS

Embodiments of the invention are described in detail in the following drawings, wherein.

DESCRIPTION OF THE PREFERRED EMBODIMENTS

Figure 1:
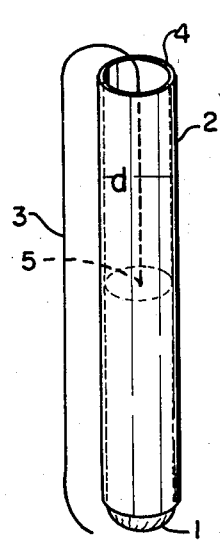
FIG. 1 shows an insertion sleeve loaded with a tampon.
Figure 7:
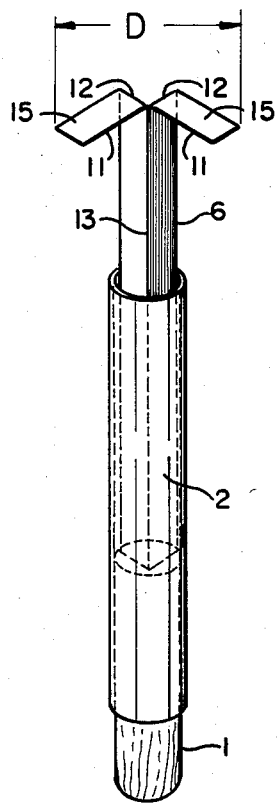
FIG. 7 shows the same insertion slide used as a plunger for pushing the tampon from the insertion sleeve.
Figure 8:
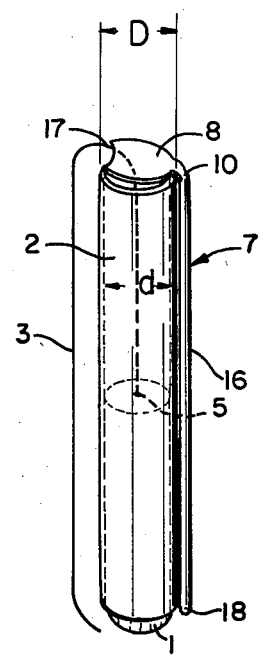
FIG. 8 shows an insertion slide in the form of a rod integrally formed at its side with an offset end plate combined with an insertion sleeve in the packaged state.

FIG. 1 shows a catamenial or surgical tampon 1 in a tubular or cylindrical insertion sleeve 2, the recovery thread 3 of the tampon 1 hanging out of the rear longitudinal end 4 of the insertion sleeve. In use, the tampon 1 is intended to be pushed out of the insertion sleeve 2 by means of a plunger which strikes the rear end 5 of the tampon. The insertion slide is preferably formed by a strip of flexible flat material, such as plastic, coated paper, laminate, or cardboard, generally denoted by the reference 6 in FIG. 2 or by a plunger-like rod generally denoted by the reference 7 with an offset end plate 8 integrally formed as shown in FIG. 8. In either case, it is essential that the rear longitudinal ends 8 or 9—remote from the tampon 1—of the insertion slide 6 or 7 respectively, should have an external diameter D which, in use, exceeds the internal diameter d of the insertion sleeve 2, but which minimally affects the volume of the package (FIG. 7).

In the first embodiment shown in FIGS. 2 to 6, the insertion slide is formed from a rectangular strip 6 of flat material, which is designed to be folded substantially along its central longitudinal axis 13 and to spread open at its rear longitudinal end 9. The width W of the strip 6 should be not more than twice the internal diameter d of the insertion sleeve 2, so that when the strip 6 is folded along its central longitudinal axis 13 it can be inserted within the sleeve 2. The length of the insertable portion L of the strip 6 should be not longer than the length of the sleeve 2. As illustrated, the strip 6 of flat material is cut substantially centrally of its longitudinal axis 13 at its rear longitudinal end 9 over a length L' substantially corresponding to the width W of the strip and, in use, is folded open transversely of the at least partially cut line 11. The at least partial cut of line 11 may be effected by dot or linear perforations, or line 11 may be completely cut. The second (transverse) foldline 12 and the first (center) fold-line 13 of the strip 6 may be perforated or embossed.

An approx. 85 mm long and approx. 10 to 14 mm wide strip of cardboard may be used for making a strip 6 of flat material suitable for inserting a catamenial tampon of regular size. To increase rigidity, the cardboard may consist of several layers pasted together with a water-soluble paste or may be laminated with a plastic. If the insertion slide is to be disposable, it is best made of a material which softens and disintegrates in water, such as cardboard.

Figure 2:
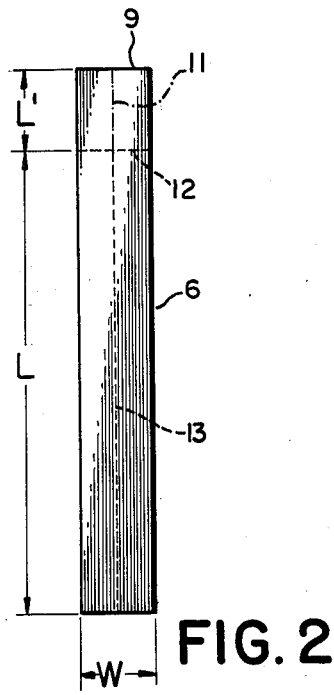
FIG. 2 shows a flat strip-form insertion slide.
Figure 3:
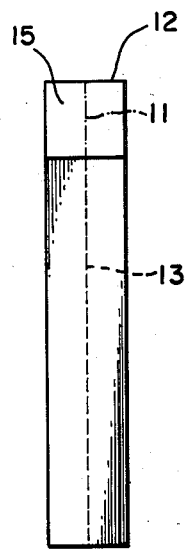
FIG. 3 shows the same insertion slide transversely folded.
Figure 4:
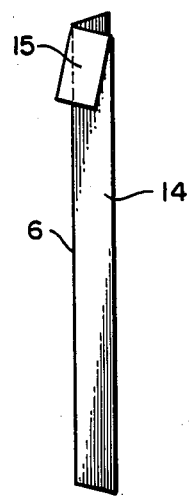
FIG. 4 shows the same insertion slide folded lengthwise and transversely.
Figure 5:
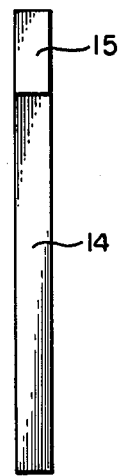
FIG. 5 shows the same insertion slide folded flat.
Figure 6:
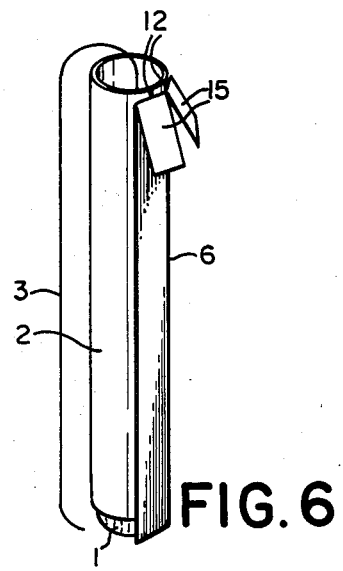
FIG. 6 shows the same insertion slide combined with the insertion sleeve shown in FIG. 1 in the packaged state.

At the production stage (or in use), the strip of flat material shown in FIG. 2 is first folded over along the second (transverse) fold-line 12 as shown in FIG. 3. The strip is then folded along its first (center) fold-line 13 as shown in FIGS. 4 and 5 and packed together with the tampon and its insertion sleeve as shown in FIG. 6. When packed, the strip 6 may either be partially folded as shown in FIG. 4 or completely folded as shown in FIG. 5. The insertion slide 6 applied flat to the outside of the sleeve 2 may optionally be fixed by a spot of glue or other fixing mechanism, for example groove-like gripping aids provided on the insertion sleeve. The overall package volume of the tampon 1 with the insertion sleeve 2 is not significantly increased by the insertion slide 6 according to the invention. In particular, there is virtually no increase in length.

The use of the insertion slide 6 shown in FIGS. 2 to 6 is diagrammatically illustrated in FIG. 7. The folded longitudinal halves 14 are pulled slightly apart and, at the same time, the tabs 15 folded over along the second fold-line 12 are separated along the at least partially cut line 11 and are turned up. The tabs 15 are thus butterflied to a wingspan D which prevents the insertion slide 6 from sliding into the insertion sleeve 2 upon ejection of the tampon 1, since D is greater than d. In the embodiment illustrated in FIG. 7, a recovery thread 3 may be inserted into the V-shaped fold between the two longitudinal halves 14 and folded over rearwards between the two down-turned tabs 15. Any absence of the recovery thread is thus immediately noticed. Accordingly, handling is simple and safe.

Another embodiment is illustrated in FIG. 8. In this case, the insertion slide 7 consists of a rod 16 with a lateral, integrally formed offset end plate 8 which functions as a finger depression at its rear longitudinal end 10. The diameter D of the finger depression 8 should be greater than the internal diameter d of the insertion sleeve 2. For a tampon, the finger depression 8 preferably has an opening 17 for insertion or guiding of the recovery thread 3. On insertion, the recovery thread is able to slide over the opening 17 and can thus be kept under observation.

The offset end plate 8 is arranged with its edge on the rear end 10 of the rod 16. This asymmetrical connection is provided to ensure a space-saving arrangement of the insertion sleeve 2 and the insertion slide 7 at the packaging stage. The front end 18 of the insertion slide 7 or rod 16 which, in use, comes into contact with the rear longitudinal end 5 of the tampon should have no sharp edges so as not to damage the tampon 1 and/or the wall of the organ into which the tampon is to be inserted, although it may widen so as to afford greater surface area to bias against the tampon or suppository.

I claim:

1. A tampon or suppository insertion applicator comprising:
   an open ended cylindrical insertion sleeve adapted to receive a tampon or suppository removably placed within it and biasing against its inner wall; and
   an ejection slide for insertion into said sleeve comprising an extended insertion member whose inserting diameter is less than that of the inner diameter of said sleeve, whose front end is adapted to bias against said tampon or suppository, and whose rear end comprises means for preventing the further insertion of said slide into said sleeve, the insertable length of said slide being not substantially greater than that of said sleeve, said ejection slide comprising a single strip of flat material which is substantially rectangular, having a short dimension less than twice the inner diameter of said sleeve and a long dimension at least equal to the length of said sleeve, said stip having a first fold line along the central axis of its long dimension, a second fold line transversing said first fold line at about a 90° angle and at a distance from the rear end of said strip approximately equal to the length of its short dimension, the portion of said first fold line between said second fold line and said rear end being at least partially cut; said further insertion preventing means being afforded when said strip is folded inward along the first fold line, folded outward along the second fold line, and said partially cut portion is completely separated, forming a butterfly whose wingspan is greater than the inner diameter of said sleeve.

2. An applicator package comprising a tampon or suppository received in an inserting sleeve and an ejection slide arranged laterally on the outside of said insertion sleeve, so that the overall length and volume of said package is not substantially greater than that of said insertion sleeve and received tampon or suppository, said insertion sleeve and said ejection slide both being in accordance with claim 1.

3. A tampon or suppository insertion applicator comprising:
   an open ended cylindrical insertion sleeve adapted to receive a tampon or suppository removably placed within it and biasing against its inner wall; and
   an ejection slide for insertion into said sleeve comprising an extended insertion member whose inserting diameter is less than that of the inner diameter of said sleeve, whose front end is adapted to bias against said tampon or suppository, and whose rear end comprises means for preventing the further insertion of said slide into said sleeve, the insertable length of said slide being not substantially greater than that of said sleeve, said ejection slide comprising an insertion rod whose length is not substantially greater than the length of said insertion sleeve, whose front end is expanded, and whose further insertion prevention means comprises an integrally formed offset plate at the rear end of said rod of sufficient size as to prevent said rear end from insertion into said sleeve.

4. The insertion applicator of claim 3 wherein said offset plate comprises a finger depression having an opening along its edge capable of receiving and guiding a recovery thread depending from the rear end of a tampon and extending out the rear end of said sleeve.

5. The insertion applicator of claim 4 wherein said sleeve receives a catamenial or surgical tampon.

6. The insertion applicator of claim 3 wherein said sleeve receives a suppository, said front end of said rod is widened to affort greater biasing surface area, and said offset plate comprises a finger depression.

7. An applicator package comprising a tampon or suppository received in an insertion sleeve and an ejection slide arranged laterally on the outside of said insertion sleeve, so that the overall length and volume of said package is not substantially greater than that of said insertion sleeve and received tampon or suppository, said insertion sleeve and said ejection slide both being in accordance with claim 3.

* * * * *